(12) United States Patent
Coultas et al.

(10) Patent No.: US 12,097,383 B2
(45) Date of Patent: Sep. 24, 2024

(54) SYSTEMS AND METHODS FOR TREATING A BIOLOGICAL FLUID WITH LIGHT IN THE EVENT OF A BULB OUTAGE

(71) Applicant: Fenwal, Inc., Lake Zurich, IL (US)

(72) Inventors: Greg Coultas, Chicago, IL (US); Christopher J. Wegener, Libertyville, IL (US); Tanima Jahan Abedin, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 151 days.

(21) Appl. No.: 16/711,926

(22) Filed: Dec. 12, 2019

(65) Prior Publication Data

US 2020/0188685 A1 Jun. 18, 2020

Related U.S. Application Data

(60) Provisional application No. 62/779,043, filed on Dec. 13, 2018.

(51) Int. Cl.
| | | |
|---|---|---|
| *A61L 2/00* | (2006.01) | |
| *A61L 2/10* | (2006.01) | |
| *A61M 1/36* | (2006.01) | |
| *A61N 5/06* | (2006.01) | |

(52) U.S. Cl.
CPC .............. *A61N 5/06* (2013.01); *A61L 2/0005* (2013.01); *A61L 2/10* (2013.01); *A61M 1/3622* (2022.05); *A61N 2005/0627* (2013.01); *A61N 2005/065* (2013.01); *A61N 2005/0658* (2013.01)

(58) Field of Classification Search
CPC .................................... A61N 5/06; A61N 2/08
See application file for complete search history.

(56) References Cited

U.S. PATENT DOCUMENTS

| | | | |
|---|---|---|---|
| 4,321,919 A | 3/1982 | Edelson | |
| 5,360,542 A | 11/1994 | Williamson, IV et al. | |
| 5,527,704 A * | 6/1996 | Wolf, Jr. ................... | C12N 7/04 435/283.1 |
| 6,027,657 A | 2/2000 | Min et al. | |
| 6,190,609 B1 * | 2/2001 | Chapman ............ | A61M 1/3683 435/283.1 |
| 6,433,343 B1 * | 8/2002 | Cimino .................. | A61K 31/37 250/455.11 |
| 7,433,030 B2 | 10/2008 | Waldo et al. | |
| 7,479,123 B2 | 1/2009 | Briggs | |
| 9,399,093 B2 | 7/2016 | Min et al. | |
| 9,744,288 B2 | 8/2017 | Min et al. | |
| 10,088,492 B2 | 10/2018 | Wegener et al. | |
| 10,172,995 B2 | 1/2019 | Radwanski et al. | |
| 10,213,544 B2 | 2/2019 | Radwanski | |
| 10,363,355 B2 | 7/2019 | Prendergast et al. | |
| 10,434,240 B2 | 10/2019 | Abedin et al. | |

(Continued)

OTHER PUBLICATIONS

European Patent Office, "Extended European Search Report", issued in connection with European application No. 19215598.4 on May 12, 2020, 8 pages.

*Primary Examiner* — Lynsey C Eiseman
(74) *Attorney, Agent, or Firm* — Cook Alex Ltd.

(57) ABSTRACT

Methods and systems for treating a biological fluid with light are disclosed. The methods and systems include determining the light dose being delivered to a biological fluid and adjusting the duration of a treatment or the intensity of light emitted in the event of a detected light source outage.

12 Claims, 8 Drawing Sheets

(56) References Cited

U.S. PATENT DOCUMENTS

| | | |
|---|---|---|
| 10,518,020 B2 | 12/2019 | Min et al. |
| 10,556,053 B2 | 2/2020 | Abedin et al. |
| 10,751,433 B2 | 8/2020 | Crawley et al. |
| 10,886,022 B2 | 1/2021 | Ali et al. |
| 10,980,933 B2 | 4/2021 | Prendergast et al. |
| 11,090,397 B2 | 8/2021 | Min |
| 11,311,823 B2 | 4/2022 | Kusters et al. |
| 11,318,239 B2 | 5/2022 | Ali et al. |
| 2003/0155531 A1* | 8/2003 | Clark ................ A61L 2/24 250/492.1 |
| 2003/0165398 A1* | 9/2003 | Waldo ............... C02F 1/325 422/22 |
| 2004/0132002 A1* | 7/2004 | Streeter ............ A61N 5/0613 435/2 |
| 2008/0234670 A1* | 9/2008 | Rogers ............... A61N 5/06 606/12 |
| 2009/0010806 A1 | 1/2009 | Hlavinka et al. |
| 2015/0028228 A1* | 1/2015 | Almasy ............... A61L 2/10 250/492.1 |
| 2016/0114095 A1 | 4/2016 | Radwanski |
| 2017/0028121 A1* | 2/2017 | Manzella ........... A61M 1/0272 |
| 2017/0029776 A1 | 2/2017 | Cork et al. |
| 2017/0197023 A1 | 7/2017 | Radwanski et al. |
| 2018/0078694 A1 | 3/2018 | Abedin et al. |
| 2019/0099544 A1 | 4/2019 | Abedin |
| 2019/0224494 A1 | 7/2019 | Radwanski et al. |
| 2020/0107765 A1 | 4/2020 | Abedin et al. |
| 2020/0222620 A1 | 7/2020 | Ali et al. |
| 2020/0297914 A1 | 9/2020 | Radwanski et al. |
| 2021/0154390 A1 | 5/2021 | Radwanski et al. |

\* cited by examiner

Method 1:

Method 2:

Method 3:

SYSTEMS AND METHODS FOR TREATING A BIOLOGICAL FLUID WITH LIGHT IN THE EVENT OF A BULB OUTAGE

CROSS-REFERENCE TO RELATED APPLICATION

This application claims the benefit of and priority to U.S. Provisional Patent Application Ser. No. 62/779,043, filed on Dec. 13, 2018, the disclosure of which is incorporated herein by reference in its entirety.

FIELD OF THE DISCLOSURE

The present disclosure is directed to systems and methods for treating a biological fluid with light. More particularly, the present disclosure is directed to systems and methods for treating a biological fluid with light when a bulb outage has occurred in the irradiation device. Even more particularly, the present disclosure is directed to automated methods for adjusting the light delivered to a biological fluid undergoing a light treatment when a bulb outage has occurred in the irradiation device.

BACKGROUND

An irradiation device is particularly useful in certain treatments of biological fluids. As used herein, biological fluid refers to any fluid that is found in or that may be introduced into the body including, but not limited to, blood and blood products. As used herein, "blood product" refers to whole blood or a component of whole blood such as red blood cells, white blood cells, platelets, plasma or a combination of one or more of such components that have been separated from whole blood.

For example, an irradiation device may be used in the treatment of a blood product that has been combined with a photochemical agent for activation when subjected to light. Such photochemical agents are used, for example, in the inactivation of viruses, bacteria, and other contaminants (collectively referred to herein as "pathogens"). Photochemical agents are also used in the treatment of mononuclear cells, such as white blood cells. In the treatment of mononuclear cells, the activated agent targets the mononuclear cell itself as part of a treatment of a disease or a side effect of a mononuclear cell therapy. One such treatment of mononuclear cells (MNCs) is referred to as extracorporeal photopheresis.

In an extracorporeal photopheresis (ECP) procedure, collected MNCs are treated with a combination of UV-A light and 8-Methoxypsoralen (8-MOP). If delivered in the right dosage, this combination causes an apoptotic response in the treated MNCs. This response is the desired treatment for conditions such as Cutaneous T-Cell lymphoma (CTCL), Acute and chronic Graft versus host disease (GvHD), and Heart and Lung transplant rejection. During an extracorporeal photopheresis procedure, an MNC collection is carried out to collect MNCs to be treated. Then, 8-MOP is injected or otherwise delivered into the treatment container (which may be the MNC collection container used during MNC collection procedures) and this mixture is photoactivated in an irradiation device with UV-A light. The treated cells are then re-infused into the patient. Systems and methods for performing ECP are described in U.S. Patent Application Publication US2014/0370491 and U.S. Pat. No. 9,399,093, all of which are incorporated by reference herein in their entireties. Examples of irradiation devices useful in carrying out ECP procedures are described in U.S. Patent Application Publications US 2017/0028121, US 2017/0029776 and US 2018/0147306, all of which are also incorporated by reference herein in their entireties.

The irradiation device typically includes one or more light sources and a UV sensor(s) that measure the amount of light being delivered to the cells (i.e., biological fluid) and a controller that controls how long the UV-A light sources remain activated based on the intensity of UV-A light sensed. An algorithm integrates the UV-A light intensity over time to arrive at a total UV-A light dose emitted value (e.g., target dose). This target dose emitted value will ideally correlate to the optimal UV-A light dose received by the cells (biological fluid) to generate the desired therapeutic response.

In the event that one or more light sources (e.g., bulbs) burns out during a photoactivation procedure, it would be desirable to have the photoactivation to continue to completion so that the patient may still receive and adequate therapy. Therefore, there is a need to develop a method in which photoactivation can continue even in the event a bulb outage occurs.

SUMMARY

In one aspect, the present disclosure is directed to a method for treating a biological fluid with light. The method includes treating the biological fluid in an irradiation chamber of an irradiation device that includes an array of multiple light sources (bulbs). The method also includes determining an effective light dose for the treatment of the biological fluid based on the intensity of light delivered by the array of multiple light sources and the duration of the treatment. The method also includes sensing the light dose delivered and adjusting the amount of light delivered by the array and/or the duration of the light treatment in response to the sensing.

In another aspect, the present disclosure is directed to a device for treating a biological fluid with light. The device may include a base unit and a lid defining an irradiation chamber for receiving a biological fluid. The device may further include at least one array of multiple light sources configured to deliver a light dose to a biological fluid within said irradiation chamber. One or more sensors are arranged within the device to measure the intensity of the light being emitted by the light sources. The device includes a controller configured to receive information from the one or more sensors regarding the intensity of the light dose being emitted and, in response to such information, adjust one or more of (a) the duration of a light treatment or (b) the intensity of the light emitted by the light sources.

DETAILED DESCRIPTION OF THE EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

Figure 1:
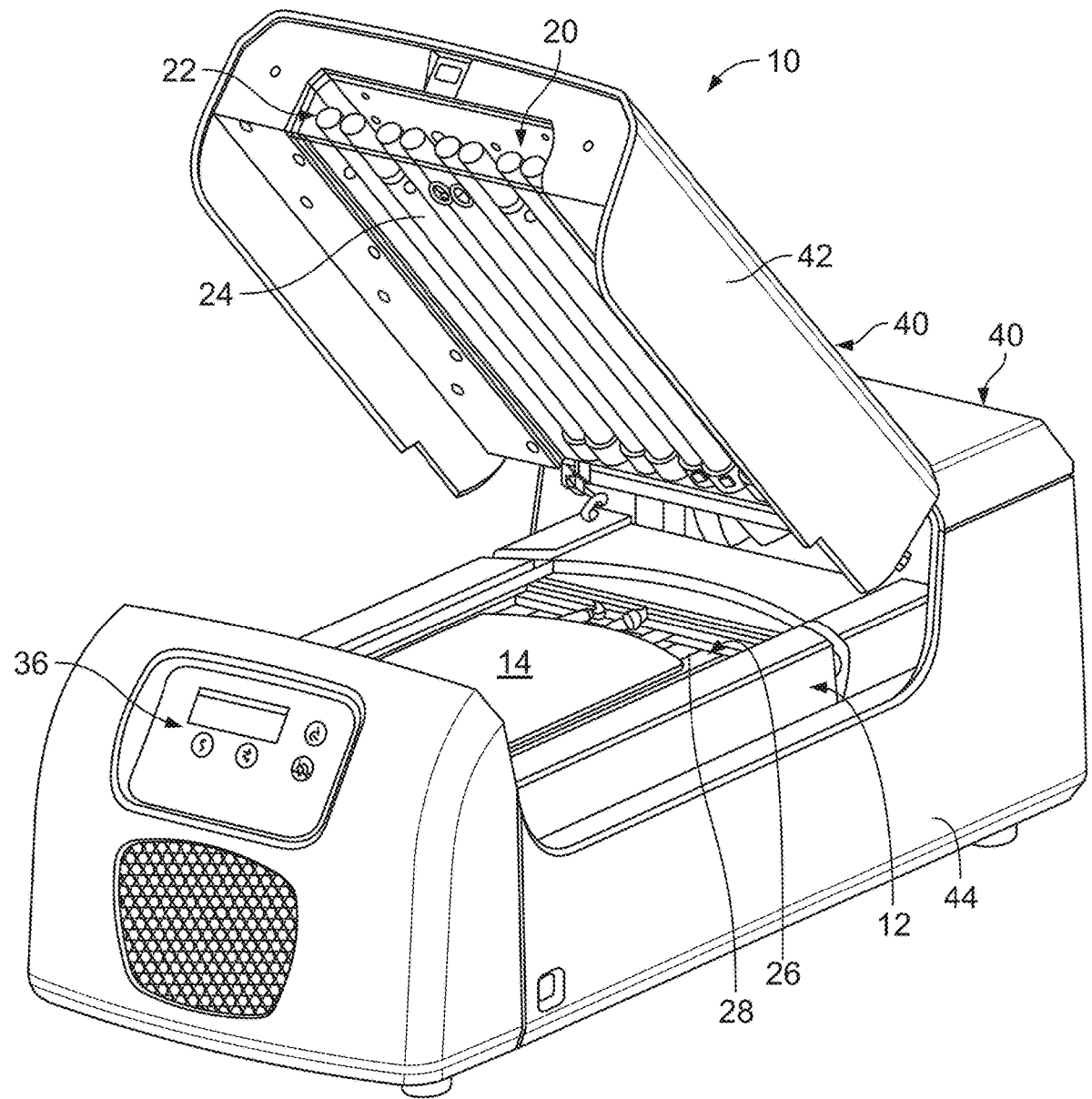
FIG. 1 is a perspective view of an embodiment of a device used to irradiate a biological fluid in a biological fluid container.
Figure 2:
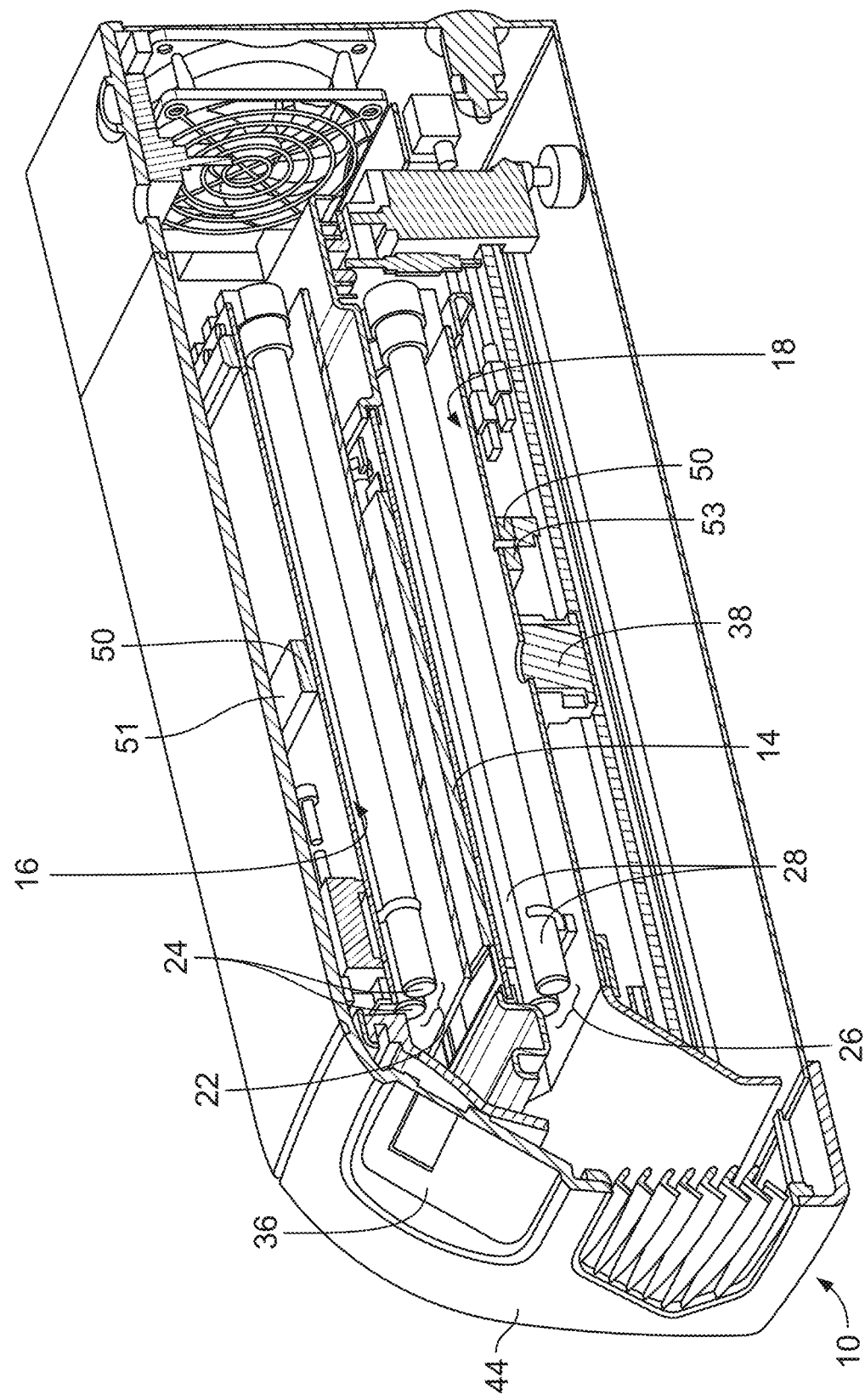
FIG. 2 is a perspective view, in cross section, of the irradiation device of FIG. 1.

As illustrated in FIG. 1, an irradiation device 10 includes a fluid treatment/irradiation chamber 12 configured to receive a biological fluid container 14, fluid treatment chamber 12 having opposing first and second sides 16, 18. As illustrated in FIGS. 1 and 2, device 10 also includes at least one light source 20 disposed adjacent at least one of first and second sides 16, 18 of fluid treatment/irradiation chamber 12. Light source 20 may include, for example, a first array 22 with a plurality of light sources 24 disposed on first side 16 of fluid treatment chamber 12 and a second array 26 with a plurality of light sources 28 disposed on second side 18 of fluid treatment chamber 12. According to an embodiment of the present disclosure, light sources 26, 28 are similar in structure and operation, and provide electromagnetic radiation in the ultraviolet portion of the spectrum (e.g., UVA). An alternative device is described in U.S. Pat. No. 7,433,030, the contents of which is incorporated by reference herein in its entirety. Device 10 may include an agitator, as shown and described in U.S. Patent Application Publication US 2017/0029776, previously incorporated by reference, coupled to fluid treatment chamber 12 to move at least a part of fluid treatment chamber 12 with an oscillatory motion. Agitator may include a motor in combination with a linkage (such as a rotating cam), the linkage coupling the motor to fluid treatment chamber 12.

As further shown in FIG. 1, device 10 may also include a housing 40 in which fluid treatment chamber 12 is defined, and in which light source 20, agitator, and other components of device 10, including one or more sensors 38 and controller 39 (described in greater detail below) are disposed. While FIG. 1 illustrates an embodiment of housing 40 including a lid 42 that may be moved pivotally relative to a base 44 to open housing 40 and permit access to fluid treatment chamber 12, it will be recognized that according to other embodiments of device 10, housing 40 may instead include a sliding drawer that permits access to fluid treatment chamber 12.

One or more sensors (e.g., one or more of a UV sensor, a hematocrit sensor, a volume or weight detector or scale, a viscosity detector, a temperature sensor, an air detector, and a density detector) are disposed within the fluid treatment chamber for measuring a condition of the biological fluid in the fluid container 14. Preferably, the sensors are mounted within or near the fluid treatment chamber in proximity to the fluid being treated. According to different embodiments, a single sensor may be provided, or a plurality of sensors may be provided to measure the various sensed conditions.

Figure 3:
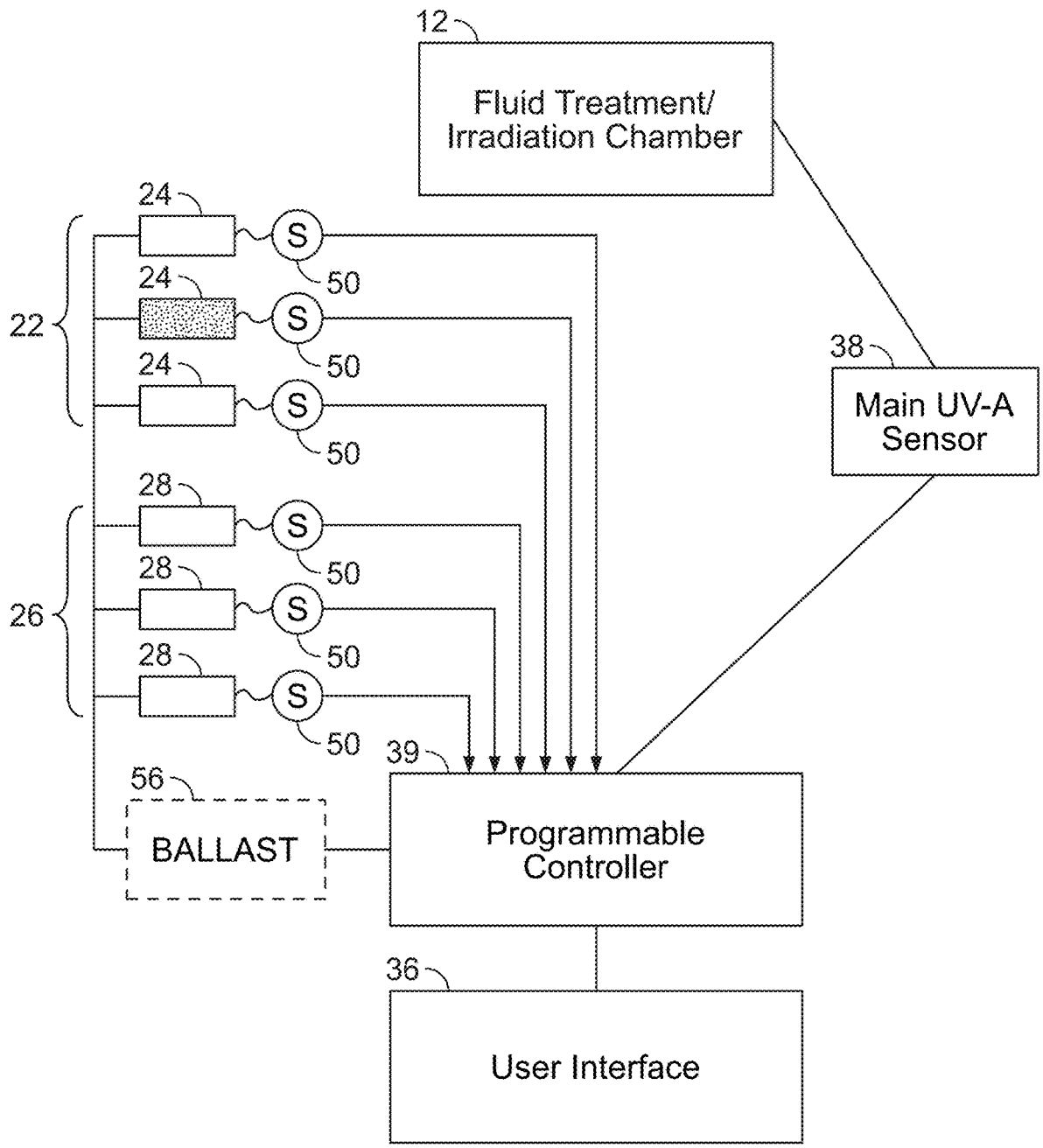
FIG. 3 is a block diagram of an embodiment of the electronic components of the irradiation device of FIG. 1 or ECP system generally.

In one embodiment, one or more light energy sensors (e.g., PMA1110-F from Solar Light Technologies) is/are disposed within or near the fluid treatment chamber for measuring the intensity of the light being delivered and ultimately the amount of light energy (dose) to which the fluid container 14 is subjected. Preferably, the light energy sensors are mounted within the fluid treatment chamber in relative proximity to the fluid container so as to more accurately determine the light energy reaching the fluid container 14 and, thus, whether or not the biological fluid has been sufficiently treated. According to different embodiments, a single "main" sensor 38 may be provided (seen in FIG. 2), and/or a plurality of additional sensors may be provided. For example, in accordance with the present disclosure, in addition to a single main light energy sensor 38, each of the individual light sources 24 (bulbs) of arrays 22 and 26 may be coupled to a sensor 50. As shown in FIG. 2, a board 51 carrying a sensor 50 for each individual bulb is centered over each bulb 24 of array 22. Similarly, board 53 carries sensors centered over each bulb 28 of array 26. FIG. 3 schematically shows each light source 24, 28 within each array 22, 26 coupled it its own sensor 50 that monitors the output of the particular light source 24, 28. As further seen in FIG. 3, each sensor 50 is likewise coupled to controller 39. Thus, as shown in FIG. 3, main light sensor 38 and/or individual light sensors 50 may be coupled to controller 39.

Controller 39 may take the form of one or more electrical components or circuits, and comprises a processor and an associated memory according to one embodiment. According to such an embodiment, the processor may be programmed to carry out any of the actions that controller 39 is described as being configured to perform below. The instructions by which the processor is programmed may be stored on the memory associated with the processor, which memory may include one or more tangible non-transitory computer readable memories, having computer executable instructions stored thereon, which when executed by the processor, may cause the one or more processors to carry out one or more actions.

As an example, the controller 39 may be programmed to carry out the following embodiment of a method of operating device 10, as explained with reference to FIGS. 1-6. In particular, controller 39 may be programmed to continue (light) treatment of a biological fluid even when one or more of light sources 24, 28 has suffered an outage or is otherwise underperforming. The term "underperforming" may include a complete outage or light source failure as well as a condition wherein the light source emits less than an optimum amount of light due to a defect in the source (bulb).

Controller 39 may be pre-programmed to effect the delivery of a selected dose of light to container 14 which includes a biological fluid that has been collected from a patient or donor. The light dose may be determined by taking into account the particular characteristics of the biological fluid to be treated such as, but not limited to, the composition of the particular biological fluid. For example, where the biological fluid is mononuclear cells (MNCs) undergoing a photodynamic therapy, the characteristics that may enter into determining the desired light dose may include the concentration of the cells, the hematocrit of the cellular product, the volume of the cellular product, the type of photoactive agent and the like. The controller will then determine the duration of the treatment based on the expected output of the light sources 24, 28 within each array 22, 26. Once the relevant information has been entered, the photodynamic therapy may commence.

As noted above, total amount of light energy to which the container of biological fluid is to be subjected during the irradiation cycle may be either preprogrammed into the controller or input by the operator through the user interface 36. The irradiation cycle may then be initiated, with the light sources 24, 28 being activated, thereby illuminating biological fluid container 14 in fluid treatment/irradiation chamber 12. The fluid container 14 is preferably oscillated by activating the agitator at the initial rate, thereby agitating biological fluid container 14 while biological fluid container 14 is illuminated.

Methods for continuing a photoactivation procedure in the event of a light source outage in accordance with the present disclosure will now be described. As described in more detail below and shown in FIGS. 7-9, the photoactivation therapy of cells or other biological fluid may be part of a larger photopheresis procedure which includes the withdrawal of a biological fluid such as blood form a patient and the separation of blood into its components, including the component to be treated.

Figure 4:
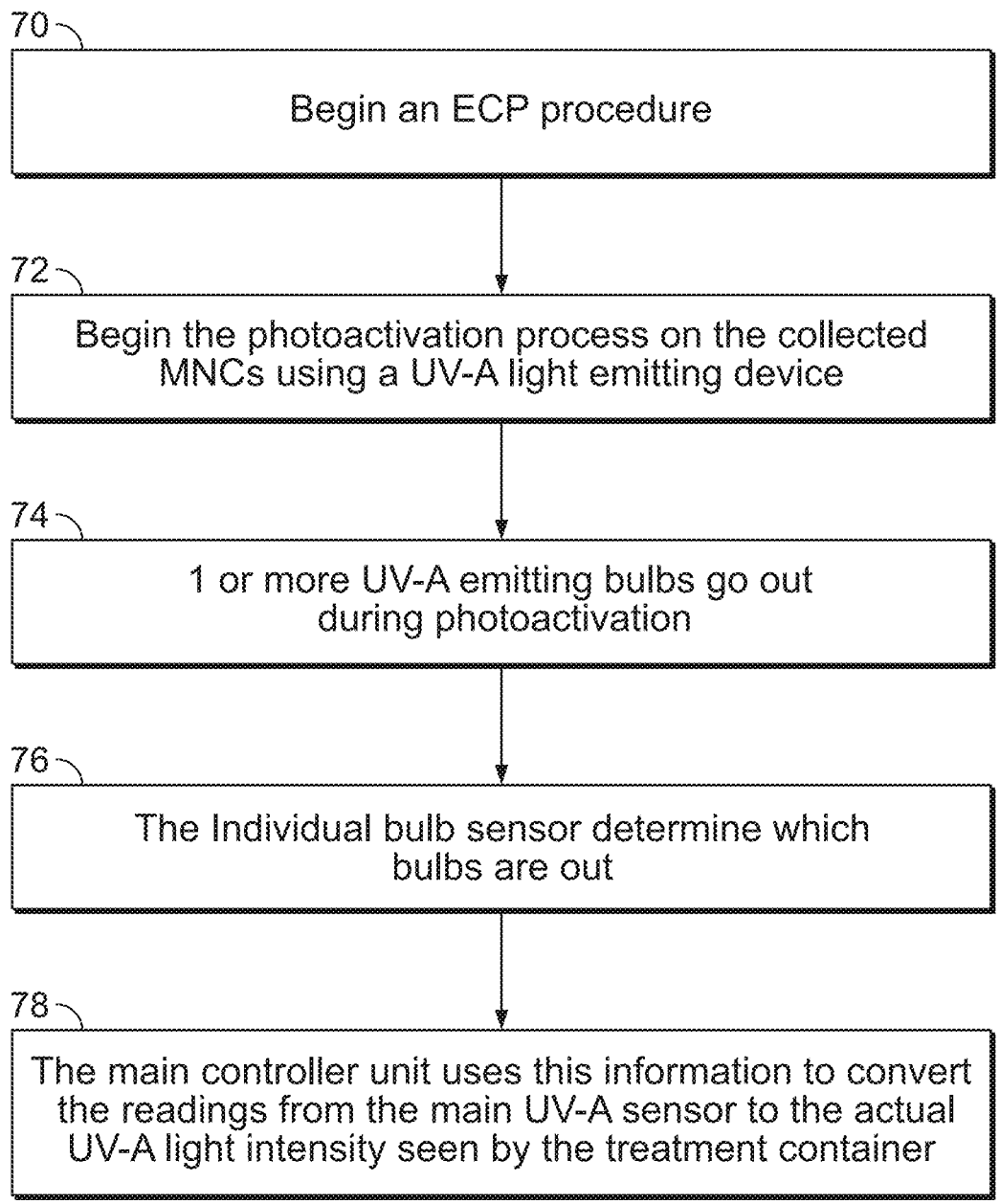
FIG. 4 is a flow diagram depicting one method of continuing a photoactivation therapy in the event of a light source outage.

Thus, as shown in FIG. 4, the first step may include the initiation of the extracorporeal photopheresis (ECP) procedure, (block 70). Once the desired cellular product has been collected and resides in collection container 14, the photoactivation process may begin (block 72). In the event of a light source outage during photoactivation (74), sensor 50 coupled to light source 22 (darkened bulb in FIG. 3) that is the subject of the outage or underperformance will send a signal to controller 39. There exists a correlation between what the main UV-A sensor 38 detects and what each light source contributes to the overall intensity and what each light source contributes to container 14 as detected by main sensor 38 which takes into account, among other things, the geometry of the fluid treatment/irradiation chamber and the location of the affected light source 22 relative to main sensor 38. Thus, the software will then convert the "reduced" main UV-A sensor 38 readings to the actual light dose being delivered to the treatment container 14 (step 76). Controller 39 will then cause remaining (properly functioning) light sources 24, 28 to remain on for a longer period of time and extend the duration of the treatment in order to reach the intended light dose (step 78).

In an alternative embodiment, the manner in which the lost contribution of the light source 22 that is the subject an outage is compensated is set forth in FIG. 5 and described below. Initially, the collection of the biological fluid and initiation of the photoactivation proceeds in a manner similar to that which is shown in FIG. 4. For example, the initiation of the extracorporeal photopheresis (ECP) procedure is shown in block 80 of FIG. 5. Once the desired cellular product has been collected and resides in collection container 14, the photoactivation process may begin (block 82). In the event of a light source outage during photoactivation (84), sensor 50 coupled to light source 22 that is the subject of the outage (darkened bulb 22 in FIG. 3) or underperformance will send a signal to controller 39. Here, however, rather than converting the reading of main sensor 38 to what is actually being delivered to container 14, controller 39 is configured to sum the light contributions of the remaining (properly functioning) light sources 24, 28 and integrate the sum over time (step 86). Under the direction of the controller 39, the remaining (properly functioning) light sources will remain on for an extended period of time to ensure the complete treatment of the biological fluid (block 88). In accordance, with this alternative method of compensating for a bulb outage, main sensor 38 is superseded in favor of the signals from the individual sensors 50 which are utilized by controller 39 to adjust the duration of the therapy.

Figure 5:
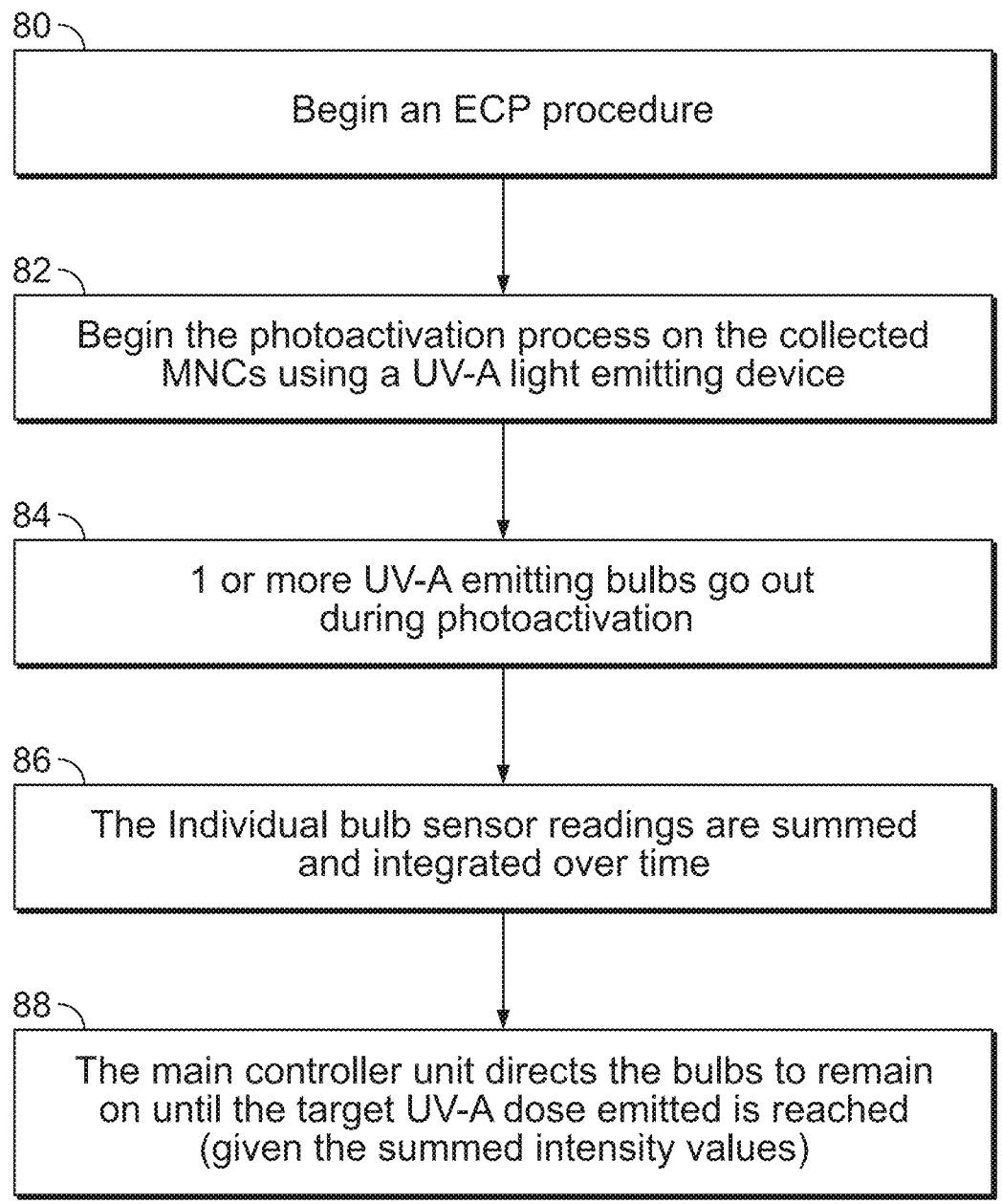
FIG. 5 is a flow diagram depicting another method of continuing a photoactivation therapy in the event of a light source outage.
Figure 6:
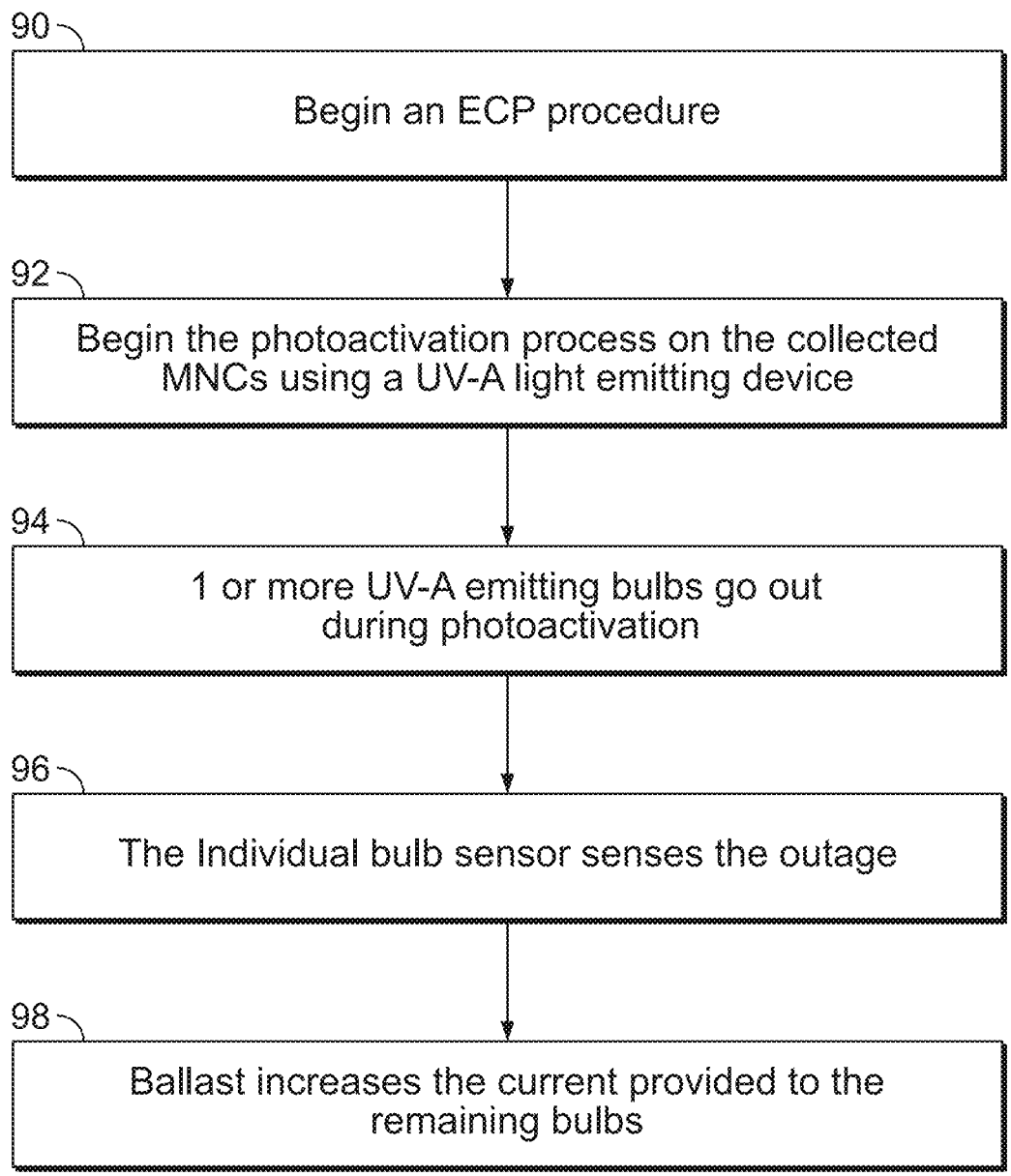
FIG. 6 is a flow diagram depicting still another method of continuing a photoactivation therapy in the event of a light source outage.

In a further alternative method of continuing with photoactivation in the event of a light source outage shown in FIG. 6, the collection of the biological fluid and initiation of the photoactivation proceed in a manner similar to that which is shown in FIGS. 4 and 5. For example, the initiation of the extracorporeal photopheresis (ECP) procedure is shown in block 90 of FIG. 6. Once the desired cellular product has been collected and resides in collection container 14, the photoactivation process may begin (block 92). In the event of a light source 24, 28 outage during photoactivation (block 94), in accordance with this further alternative method, the individual light source sensor 50 would sense which of the light sources suffered an outage and the controller 39 would determine the decrease in the total UV-A light intensity (block 96) either by the diminished overall intensity sensed by main sensor 38 (in accordance with method of FIG. 4) or by the reduced cumulative intensity of the individual bulbs (in accordance with the method of FIG. 5). Controller 39 would then instruct the ballast 56 (FIG. 3), which regulates the current to the light sources 24, 28, to increase the current to the remaining and properly functioning light sources (block 98). This would increase the intensity of the light delivered by each of the remaining light sources in order to compensate for the light source outage. With the increased intensity being delivered by each of the remaining light sources, the amount of time needed to reach the desired target may be less than in the methods described above and shown in FIGS. 4 and 5.

Photoactivation and the methods for correcting for bulb outages may be part of a larger ECP procedure (as indicated in steps 70, 80 and 90). A detailed description of an entire ECP procedure is beyond the scope of the present disclosure and, in any event, can be gleaned from U.S. Patent Application Publication US2014/0370491 and U.S. Pat. No. 9,399,093 both of which are incorporated by reference. However, a general overview of the ECP system is provided below.

Figure 7:
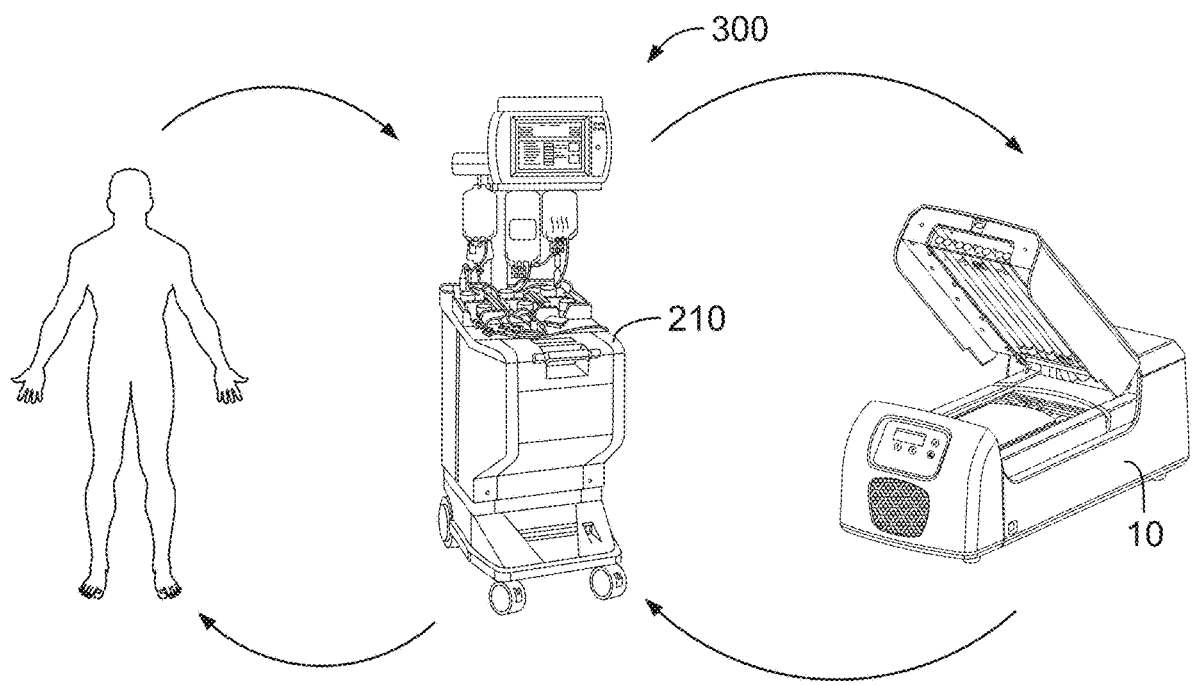
FIG. 7 is a diagram of an embodiment of a system including the irradiation device of FIG. 1 in combination with a cell separator.
Figure 8:
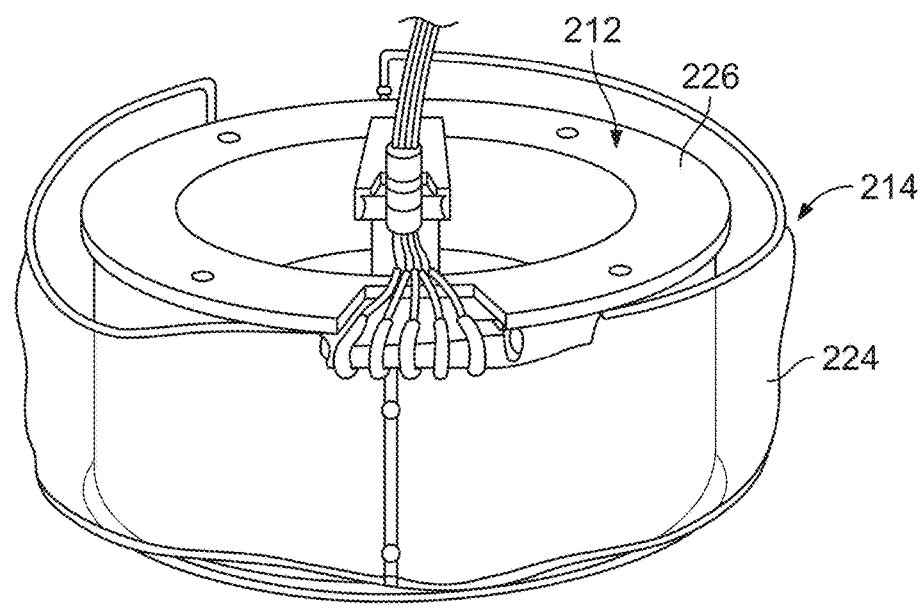
FIG. 8 is a perspective view of a processing container (separation chamber) of a processing set used with the separator of FIG. 7.
Figure 9:
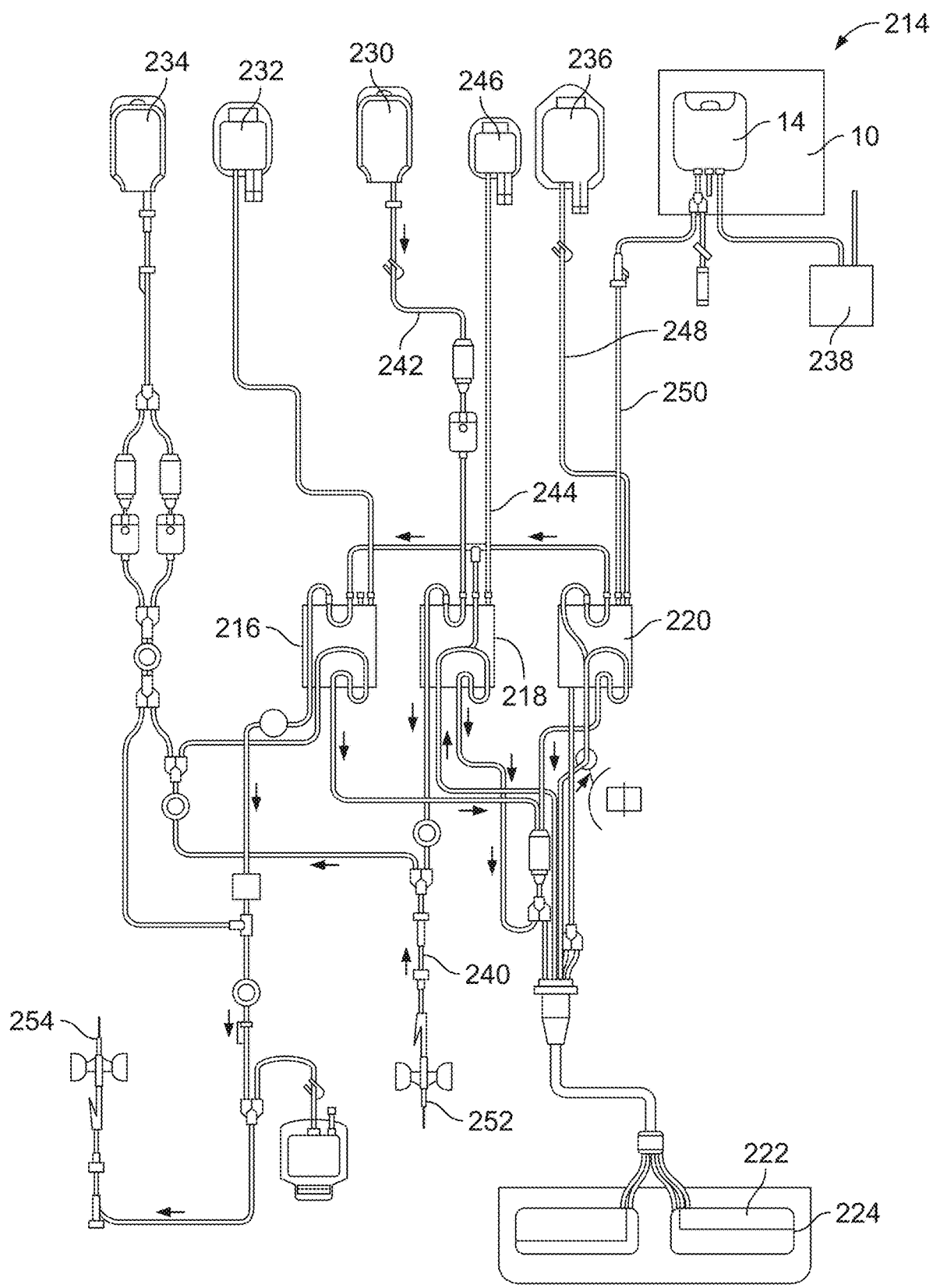
FIG. 9 is a diagram of a processing set for used with the separator of FIG. 7, including the processing container illustrated in FIG. 8.

While irradiation device 10 may be used as a stand-alone device, irradiation device 10 may also be used in conjunction with a cell separator 210 as part of a system 300, as illustrated in FIGS. 7-9. With reference to FIGS. 7-9, system 300 includes a cell separator 210 and irradiation device 10. Cell separator 210 would be configured to direct a biological fluid into a biological fluid container (e.g., container 14), and irradiation device 10 would include fluid treatment/irradiation chamber 12 configured to receive biological fluid container 14. The cell separator 210 may be an Amicus® Separator made and sold by Fenwal, Inc., of Lake Zurich, Illinois, a subsidiary of Fresenius-Kabi of Bad Homburg, Germany. Mononuclear cell collections performed using a device such as the Amicus® are described in greater detail in U.S. Pat. No. 6,027,657, the contents of which is incorporated by reference herein in its entirety.

Briefly, FIGS. 7-9 show separator 210 in FIG. 7, a representative blood centrifuge 212 (defining part of the separator 210) with a portion of a fluid circuit 214 mounted thereon in FIG. 8, and the entire fluid circuit 214 in FIG. 9. Fluid circuit (also referred to as a processing set) 214 includes a plurality of processing fluid flow cassettes 216, 218 and 220 (see FIG. 9) with tubing loops for association with peristaltic pumps on device 210. Fluid circuit 214 also includes a network of tubing and pre-connected containers for establishing flow communication with the patient and for processing and collecting fluids and blood and blood components, as shown in greater detail in FIG. 9.

As illustrated in FIGS. 8 and 9, a separation chamber 222 is defined by the walls of a flexible processing container 224 carried within an annular gap defined by a rotating spool element 226 (see FIG. 8) and an outer bowl element (not shown). The processing container 224 takes the form of an elongated tube that is wrapped about the spool element 226 before use. The bowl and spool element 226 are pivoted on a yoke between an upright position and a suspended position, also not shown. In operation, the centrifuge 212 rotates the suspended bowl and spool element 226 about an axis, creating a centrifugal field within the processing chamber of container 224. Details of the mechanism for causing relative movement of the spool 226 and bowl elements as just described are disclosed in U.S. Pat. No. 5,360,542, the contents of which is also incorporated by reference herein in its entirety.

As seen in FIG. 9, the disposable processing set 214 may include flexible processing container 224, as well as a container 230 for supplying anticoagulant, a waste container 232 for collecting waste from one or more steps in the process for treating and washing mononuclear cells, a container 234 for holding saline or other wash or resuspension medium, a container 236 for collecting plasma, container 14 for collecting mononuclear cells from the operation discussed relative to FIG. 8 and, optionally, container 238 for holding a photoactivation agent or other device (such as a syringe for delivering the agent.

Container 14 is preferably pre-attached to with the disposable set 214. Alternatively, container 14 may be attached to set 214 by known sterile connection techniques, such as sterile docking or the like. With reference to FIG. 9, fluid circuit includes inlet line 240, an anticoagulant (AC) line 242 for delivering AC from container 230, an RBC line 244 for conveying red blood cells from chamber 222 of container 224 to container 246, a platelet-poor plasma (PPP) line 248 for conveying PPP to container 236 and line 250 for conveying mononuclear cells to and from separation chamber 222 and collection/illumination container 14. The blood processing set 214 includes one or more venipuncture needle (s) for accessing the circulatory system of the patient. As shown in FIG. 9, fluid circuit 214 includes inlet needle 252 and return needle 254. In an alternative embodiment, a single needle can serve as both the inlet and outlet needle.

Container 14 is suitable for irradiation by light of a selected wavelength. By "suitable for irradiation", it is meant that the walls of the container are sufficiently translucent to light of the selected wavelength. In treatments using UVA light, for example, container walls made of ethylene vinyl acetate (EVA) are suitable. Accordingly, container 14 in which the mononuclear cells are collected may serve both as the collection container and the irradiation container. Container 14 may be placed inside irradiation device 10 by the operator or, more preferably, may be placed inside the irradiation chamber of irradiation device 10 at the beginning of a procedure including the cell separator and prior to whole blood withdrawal (as shown by the broken lines representing device 20 in FIG. 9). Preferably container 14 remains integrally connected to the remainder of fluid circuit 214 during the entire procedure, thereby maintaining the closed or functionally closed condition of fluid circuit 214.

Fluid flow through fluid circuit 214 is preferably driven, controlled and adjusted by a microprocessor-based controller in cooperation with the valves, pumps, weight scales and sensors of device 210 and fluid circuit 214, the details of which are described in the previously mentioned U.S. Pat. No. 6,027,657. In this regard, automated control of the MNC collection and the irradiation treatment may be effected by the microprocessor-based controller of the respective separation device 210 and irradiation device 10 with some operator input for each device. Alternatively, operation of both separation device 210 and irradiation device 10 and the process steps carried out by each may be remotely controlled by a separate controller (e.g., a computer) that communicates with both.

Without limiting any of the foregoing, the disclosed device, method and system may include one or more of the aspects set forth below.

OTHER EXAMPLES

Aspects of the present subject matter described above may be beneficial alone or in combination with one or more other Aspects, as described below.

Aspect 1. A method for treating a biological fluid with light including the steps of: treating a biological fluid in an irradiation chamber of an irradiation device, said device comprising at least one array of multiple light sources; determining an effective light dose for the treatment of said biological fluid based on the intensity of light delivered to said biological fluid, wherein said effective light dose is based on the biological fluid to be treated, the intensity of the light delivered by the array of multiple light sources and the duration of the treatment; sensing the light dose delivered by said at least one array; adjusting the power delivered to said array and/or the duration of the light treatment in response to said sensing.

Aspect 2. The method of Aspect 1 including detecting the light intensity of each one of said multiple light sources of said array.

Aspect 3. The method of Aspect 2 including sensing the contribution of each one of said multiple light sources of said array to the sensed light dose delivered to said biological fluid.

Aspect 4. The method of Aspect 3 including identifying an underperforming light bulb within said array.

Aspect 5. The method of Aspect 4 including determining the actual light dose delivered to said biological fluid wherein at least one of said light bulbs is underperforming.

Aspect 6. The method of Aspect 5 including adjusting the duration of said light treatment to arrive at said effective light dose.

Aspect 7. The method of Aspect 6 wherein said adjusting said duration of said treatment is based at least in part on a location of said underperforming bulb within said array.

Aspect 8. The method of Aspect 7 wherein said adjusting said duration of said treatment is based at least in part on said location of said underperforming bulb within said array and a geometry of said irradiation chamber.

Aspect 9. The method of any one of Aspects 7 through 8 including extending the duration of said treatment by extending the duration of activation of said bulbs of said array.

Aspect 10. The method of Aspect 4 including increasing the intensity of light delivered by the remaining bulbs that are not underperforming.

Aspect 11. The method of Aspect 10 including increasing said intensity by increasing current to said remaining bulbs that are not underperforming.

Aspect 12. A device for treating a biological fluid with light including: a base unit and a lid defining an irradiation chamber for receiving a biological fluid; at least one array of multiple light sources configured to deliver a light dose to a biological fluid within said irradiation chamber; one or more sensors arranged to measure the light dose being delivered; and a controller configured to receive information from said one or more sensors regarding the light dose being delivered and, in response to said information, adjust one or more of: the duration of a light treatment; the intensity of the light emitted by the light sources; and the contribution of each light source within said at least one array.

Aspect 13. The device of Aspect 12 including a sensor associated with each of said light sources of said at least one array of multiple light sources for determining the output of said each of said light sources.

Aspect 14. The device of any one of Aspects 12 and 13 further including an input for entering a predetermined effective light dose to be delivered to said biological fluid.

Aspect 15. The device of any one of Aspects 12 through 14 including a first array of light sources on one side of said irradiation chamber and a second array of light sources on the opposite side of said irradiation chamber.

Aspect 16. The device of any one of Aspects 12 through 15 wherein said controller is configured to compare a predetermined effective light dose to an actual light dose being delivered to said biological fluid.

Aspect 17. The device of any one of Aspects 13 through 16 further including a main sensor for determining the total output of said at least one array of multiple light sources.

Aspect 18. The device Aspect 17 wherein said controller is configured to receive the light dose being delivered by each of said light sources and compare the sum of such light doses to said predetermined effective light dose.

Aspect 19. The device of Aspect 18 wherein said controller is configured to adjust the duration of a light treatment based on said comparison.

Aspect 20. The device of Aspect 18 wherein said controller is configured to adjust the duration of a light treatment based on said sum of said light doses independent of information received by said main sensor.

Aspect 21. The device of any one of Aspects 12 through 20 wherein said controller is configured to increase the current to selected light sources of said at least one array of multiple light sources.

Aspect 22. The device of Aspect 21 wherein said controller is configured to increase the current to selected light sources of said at least one array of multiple light sources in response to said one or more sensors detecting an outage in at least one light source in said at least one array.

The invention claimed is:

1. A device for treating a biological fluid with light comprising:
   a) a base unit and a lid defining an irradiation chamber for receiving a biological fluid;
   b) at least one array of multiple light sources configured to deliver a light dose to a biological fluid within said irradiation chamber;
   c) a main light sensor and a plurality of individual light sensors, wherein the main light sensor is configured to sense the overall light intensity within the irradiation chamber during a treatment of a biological fluid, wherein the number of individual light sensors is equal to the number of light sources of the at least one array of multiple light sources and wherein each individual light sensor of the plurality of individual light sensors is coupled to an individual light source of the at least one array of multiple light sources, wherein each individual light sensor is configured to sense the light from the individual light source to which it is coupled; and
   d) a controller configured to receive information from said individual light sensors regarding an underperforming light source within said at least one array of multiple light sources and, in response to said information, configured to continue delivery of said light and to automatically adjust one or more of:
      i. the duration of a light treatment;
      ii. the intensity of the light emitted by the light sources of the at least one array of multiple light sources; and
      iii. the contribution of each light source within said at least one array of multiple light sources,
   based on information from the main light sensor and individual light sensors.

2. The device of claim 1, wherein the individual light sensors are configured to determine the output of said light sources of the at least one array of multiple light sources.

3. The device of claim 1 further comprising an input for entering a predetermined effective light dose to be delivered to said biological fluid.

4. The device of claim 1 comprising a first array of light sources on one side of said irradiation chamber and a second array of light sources on the opposite side of said irradiation chamber.

5. The device of claim 1 wherein said controller is configured to compare a predetermined effective light dose to an actual light dose being delivered to said biological fluid.

6. The device of claim 5, wherein said main light sensor is configured to determine the total output of said at least one array of multiple light sources.

7. The device of claim 6 wherein said controller is configured to receive the light dose being delivered by each of said light sources of the at least one array of multiple light sources and compare the sum of such light doses to said predetermined effective light dose.

8. The device of claim 7 wherein said controller is configured to adjust the duration of a light treatment based on said comparison.

9. The device of claim 7 wherein said controller is configured to adjust the duration of a light treatment based on said sum of said light doses independent of information received by said main sensor.

10. The device of claim 1 wherein said controller is configured to increase the current to selected light sources of said at least one array of multiple light sources.

11. The device of claim 10 wherein said controller is configured to increase the current to selected light sources of said at least one array of multiple light sources in response to said one or more sensors detecting an outage in at least one light source in said at least one array.

12. The device of claim 1, wherein the main light sensor is located in a first location within the irradiation chamber and the individual light sensors are centered over the individual light source to which it is coupled.

* * * * *